(12) United States Patent
Peterson et al.

(10) Patent No.: US 8,382,810 B2
(45) Date of Patent: Feb. 26, 2013

(54) TORSION CUTTER AND CANNULATED CUTTER FOR CUTTING ORTHOPEDIC FASTENERS

(75) Inventors: Scott M. Peterson, Pasadena, MD (US); William Carey, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 1001 days.

(21) Appl. No.: 12/328,039

(22) Filed: Dec. 4, 2008

(65) Prior Publication Data
US 2009/0149889 A1 Jun. 11, 2009

Related U.S. Application Data

(60) Provisional application No. 60/992,429, filed on Dec. 5, 2007, provisional application No. 61/053,143, filed on May 14, 2008.

(51) Int. Cl.
*A61B 17/86* (2006.01)
*A61B 17/58* (2006.01)
*B25B 15/02* (2006.01)
*F16B 31/00* (2006.01)

(52) U.S. Cl. ............... 606/306; 606/104; 81/461; 411/2

(58) Field of Classification Search .................. 606/300, 606/301, 305–310, 331, 104, 86 B, 174; 411/1–5; 81/437, 451, 456, 461, 9.24, 55, 124.5
See application file for complete search history.

(56) References Cited

U.S. PATENT DOCUMENTS

| 3,498,351 | A | * | 3/1970 | Edwards et al. ................ 81/453 |
| 4,462,403 | A | | 7/1984 | Martin |
| 4,466,315 | A | * | 8/1984 | Boschetto et al. .............. 81/437 |
| 5,328,361 | A | | 7/1994 | Ezcurra |
| 5,419,047 | A | | 5/1995 | Farzin-Nia |
| 5,624,216 | A | * | 4/1997 | Detable et al. .................... 411/5 |
| 5,822,865 | A | | 10/1998 | Bosch et al. |
| 6,066,143 | A | | 5/2000 | Lane |
| 6,077,267 | A | * | 6/2000 | Huene ........................... 606/916 |
| 6,159,179 | A | | 12/2000 | Simonson |
| 6,517,545 | B1 | | 2/2003 | Mazur |
| 6,672,791 | B2 | * | 1/2004 | Schubring et al. ............ 403/296 |
| 6,673,078 | B1 | | 1/2004 | Muncie |
| 6,702,820 | B2 | | 3/2004 | Mazur |
| 6,730,089 | B2 | * | 5/2004 | Jackson ........................ 606/270 |
| 6,860,017 | B1 | | 3/2005 | Mennicken |
| 7,257,897 | B2 | | 8/2007 | Li et al. |
| 2003/0158556 | A1 | * | 8/2003 | Taras et al. ..................... 606/73 |
| 2007/0106283 | A1 | * | 5/2007 | Garcia et al. ...................... 606/1 |

* cited by examiner

*Primary Examiner* — Thomas Barrett
*Assistant Examiner* — Michael T Schaper
(74) *Attorney, Agent, or Firm* — Carlson, Gaskey & Olds, P.C.

(57) ABSTRACT

A surgical instrument includes a first component and a second component moveable about an axis relative to the first component. The second component is moveable between a first position and a second position. Movement of the second component from the first position to the second position applies a torsional force to an orthopedic fastener to remove a portion of the orthopedic fastener.

15 Claims, 16 Drawing Sheets

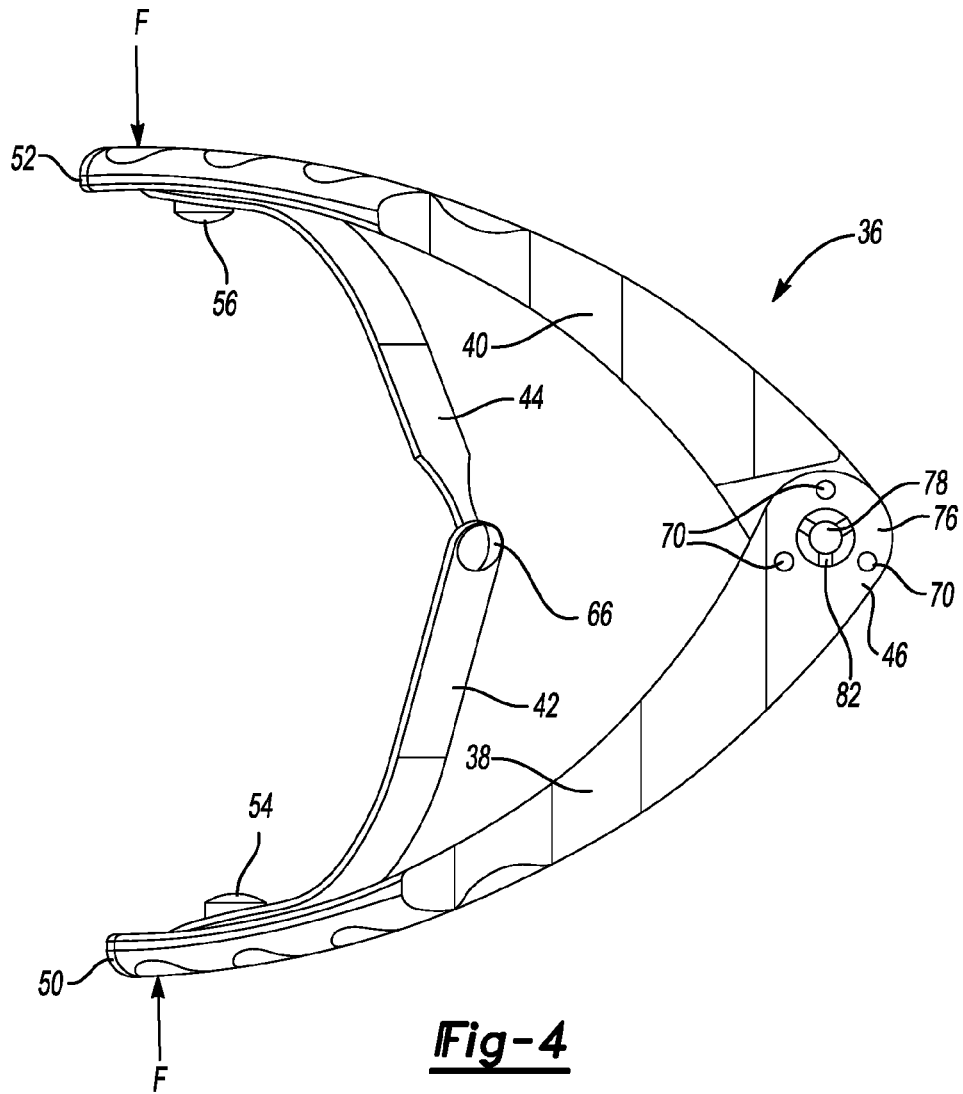
_Fig-4_
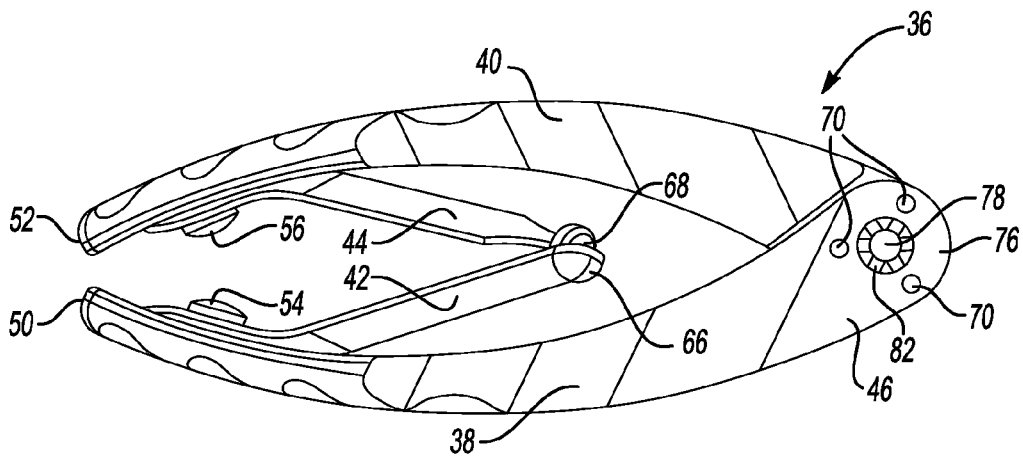
_Fig-5_

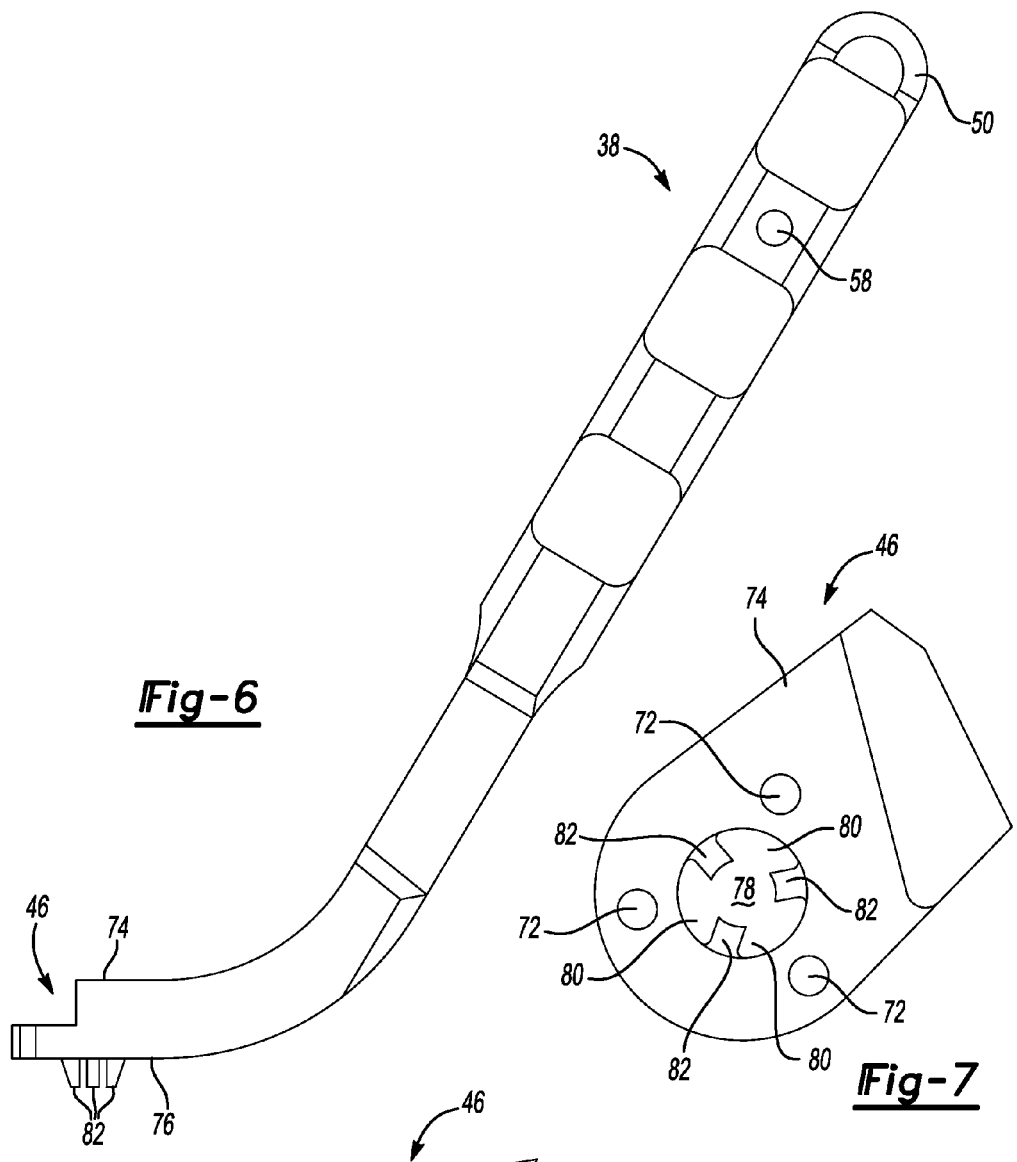
*Fig-6*
*Fig-7*
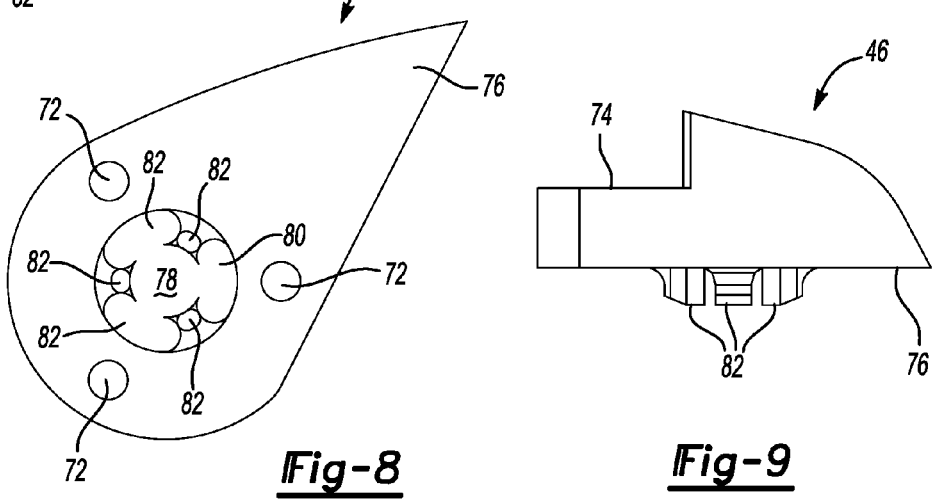
*Fig-8*
*Fig-9*

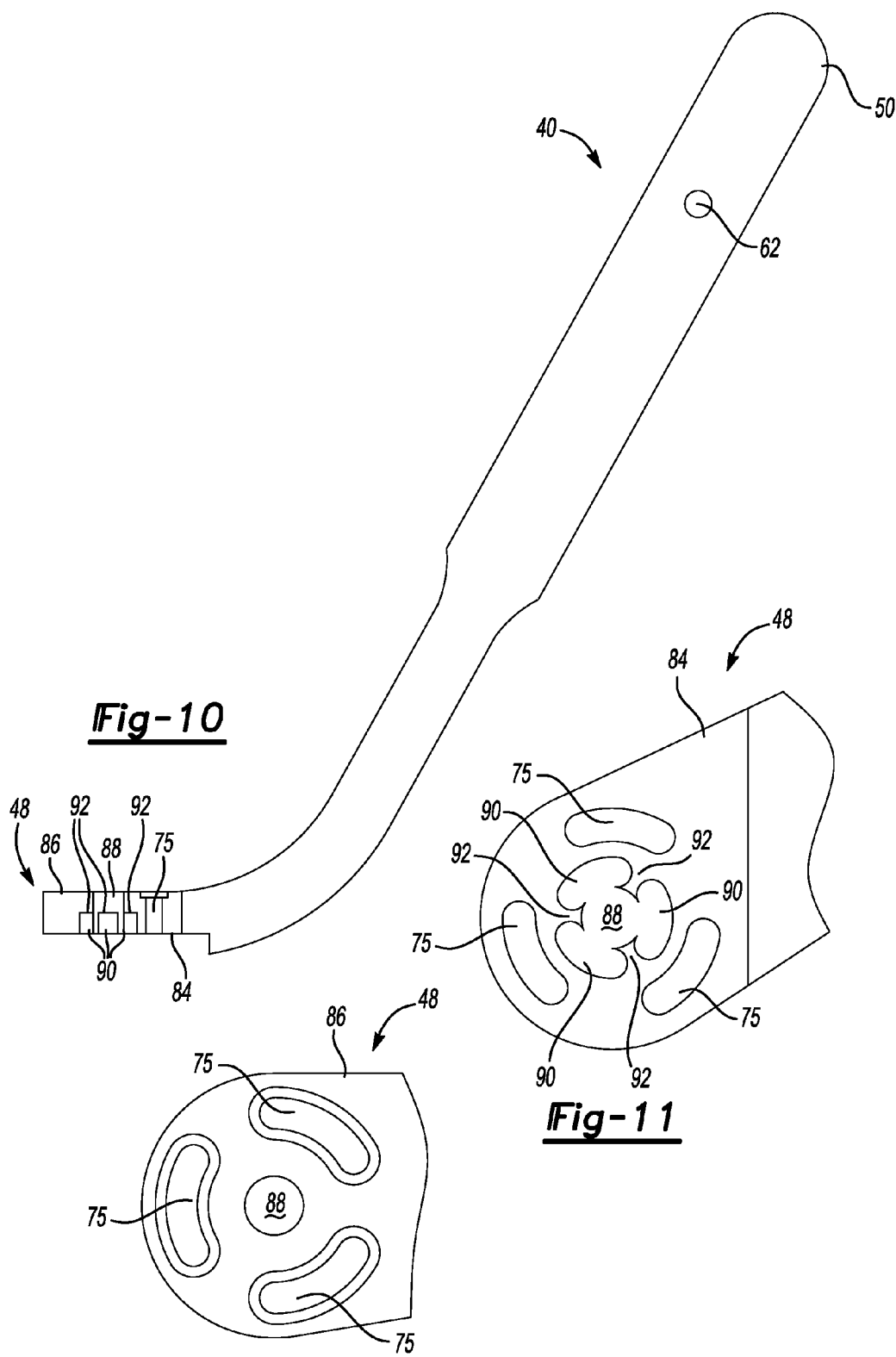

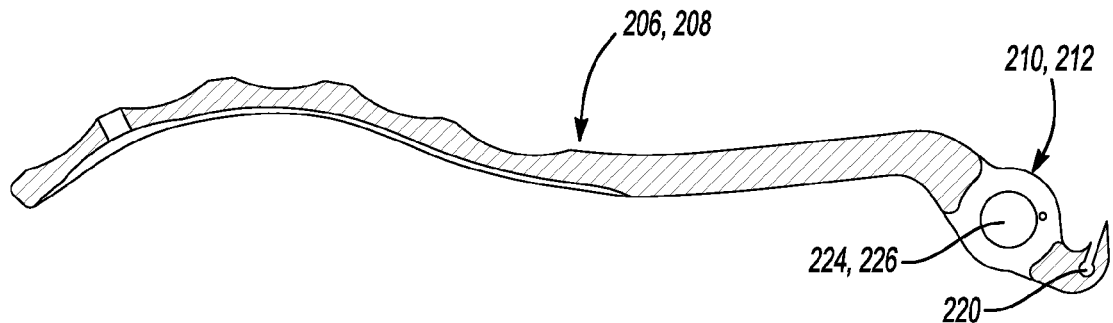
Fig-24
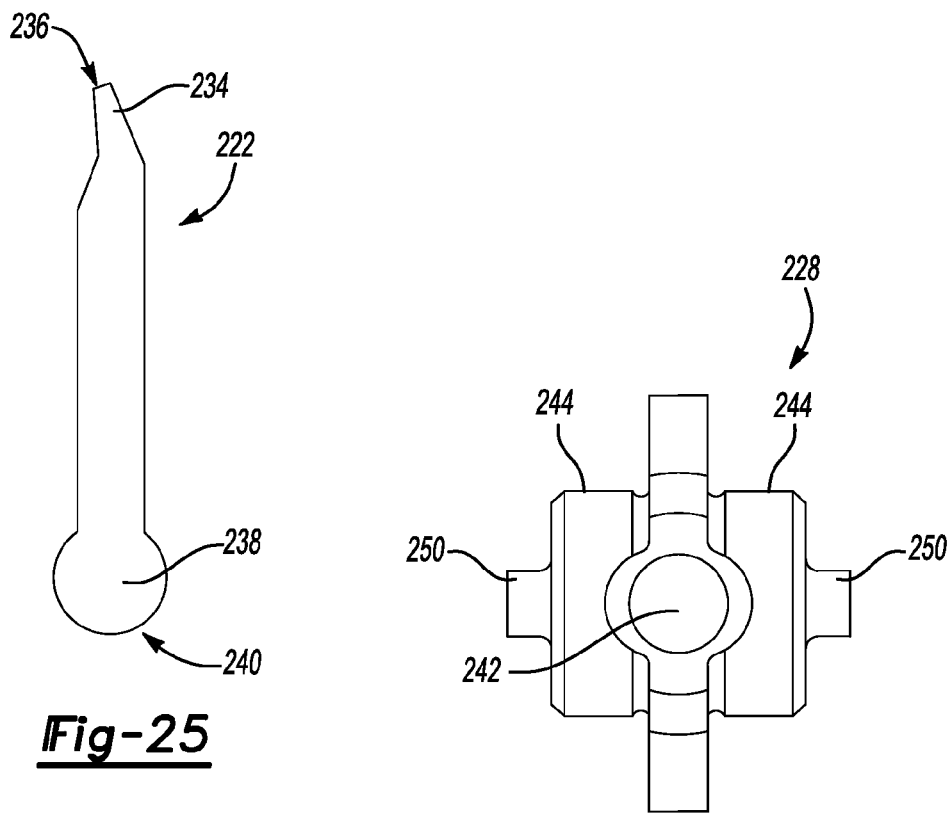
Fig-25
Fig-27

TORSION CUTTER AND CANNULATED CUTTER FOR CUTTING ORTHOPEDIC FASTENERS

REFERENCE TO RELATED APPLICATIONS

This application claims priority to U.S. Provisional Patent Application No. 60/992,429 filed Dec. 5, 2007 and U.S. Provisional Patent Application No. 61/053,143 filed May 14, 2008.

BACKGROUND OF THE INVENTION

This application relates generally to a surgical instrument, and more particularly, to a torsion cutter or a cannulated cutter, for cutting an orthopedic fastener or the like.

Orthopedic surgery requires the use of a multitude of surgical instruments including, but not limited to, cutters, drills, anchors, etc. Cutters are often required to trim orthopedic fasteners, such as pins, screws, wires or the like, that may protrude from a patient's bone. For example, during an osteotomy to correct bunions, a surgeon makes a cut in a patient's bone and removes a segment of the bone. The patient's bones are then realigned and pinned in place with an orthopedic fastener. The orthopedic fastener is typically left within the bone until the bone heals so that the underlying bone deformity is corrected and the bunion will not reoccur. The orthopedic fastener will often include an excess portion that protrudes from the bone and requires trimming.

Orthopedic cutters are known that are capable of trimming orthopedic fasteners and the like. These cutters typically include a pair of handles and a pair of opposing jaws that each include a cutting tip. The cutting tips are relatively large and include beveled surfaces on each side of the cutting tip to increase the strength of the cutting tip. Disadvantageously, known surgical cutters leave a substantial burr on the orthopedic fastener after the cut is made. If the orthopedic fastener is left in/on the patient, the cut surface is covered with a plastic cap to avoid irritation caused by the sharp burr. This may add additional time and expense to the surgical procedure. Additionally, where a relatively large amount of excess fastener material protrudes from the bone, multiple cuts must be made to the orthopedic fastener. This may further slow the surgical procedure.

SUMMARY OF THE INVENTION

A surgical instrument includes a first component and a second component moveable about an axis relative to the first component. The second component is moveable between a first position and a second position. Movement of the second component from the first position to the second position applies a torsional force to an orthopedic fastener to remove a portion of the orthopedic fastener.

In another illustrative example, a surgical instrument includes a first component and a second component rotatable relative to the first component about a rotational axis. The second component is rotatable between a first position and a second position. Rotation of the second component from the first position to the second position applies a force to an orthopedic fastener to remove a portion of the orthopedic fastener. A central axis of the orthopedic fastener is aligned with the rotational axis.

These and other features of the present invention will be best understood from the following specification and drawings.

BRIEF DESCRIPTION OF THE DRAWINGS

The various features and advantages of this disclosure will become apparent to those skilled in the art from the following detailed description. The drawings that accompany the detailed description can be briefly described as follows:

FIG. 4 illustrates the first embodiment torsion cutter in an open position;

FIG. 5 illustrates the first embodiment torsion cutter in a closed position;

FIG. 6 illustrates a side view of a first hand grip;

FIG. 7 illustrates an inner surface of a twisting portion of the first hand grip;

FIG. 8 illustrates an outer surface of the twisting portion of the first hand grip;

FIG. 9 illustrates an enlarged side view of the twisting portion of the first hand grip;

FIG. 10 illustrates a side view of a second hand grip;

FIG. 11 illustrates an inner surface of the twisting portion of the second hand grip;

FIG. 12 illustrates an outer surface of the twisting portion of the second hand grip;

FIG. 24 illustrates a portion of a handle assembly of the cannulated cutter;

FIG. 25 illustrates a cutting tip of the cannulated cutter;

FIG. 27 illustrates a swivel pin of the cannulated cutter;

DETAILED DESCRIPTION OF THE DISCLOSED EMBODIMENT

Figure 1:
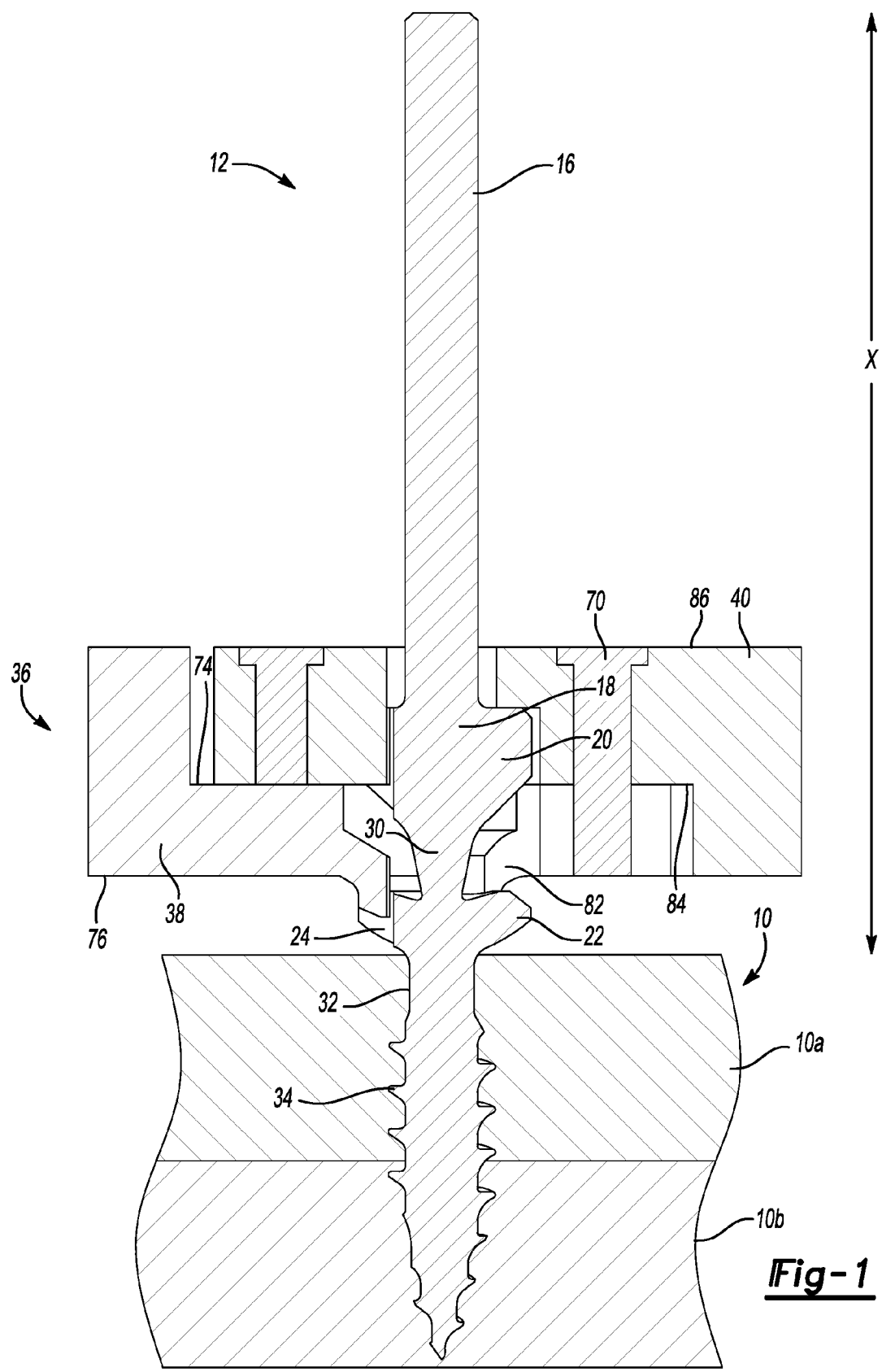
FIG. 1 illustrates a schematic representation of a surgical procedure for correcting a bone deformity employing a first embodiment torsion cutter.
Figure 16:
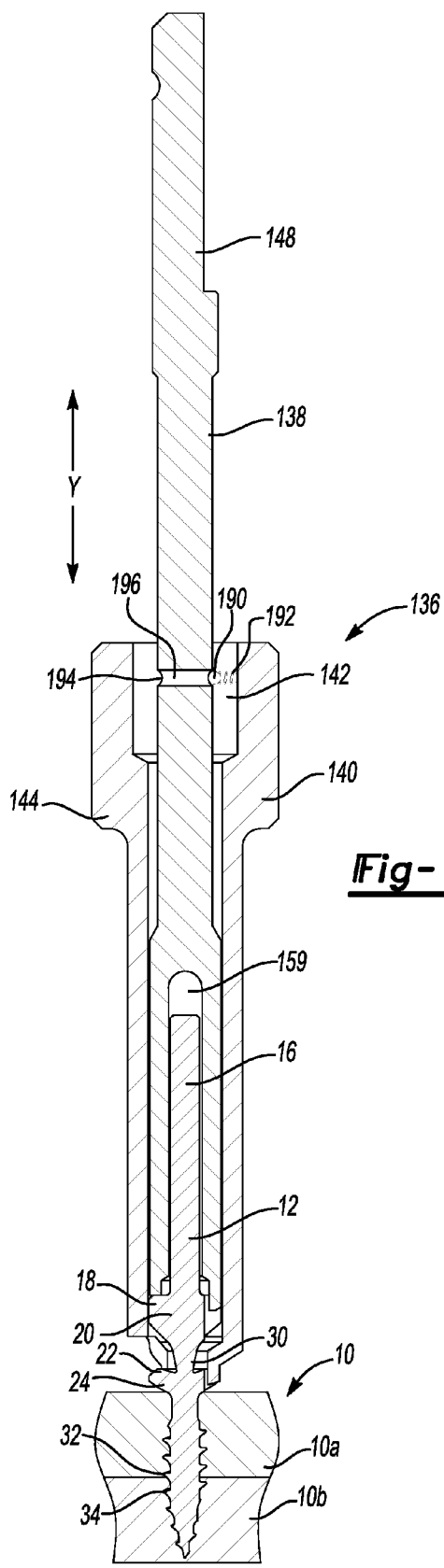
FIG. 16 illustrates a schematic representation of a surgical procedure for correcting a bone deformity employing a second embodiment torsion cutter.
Figure 21:
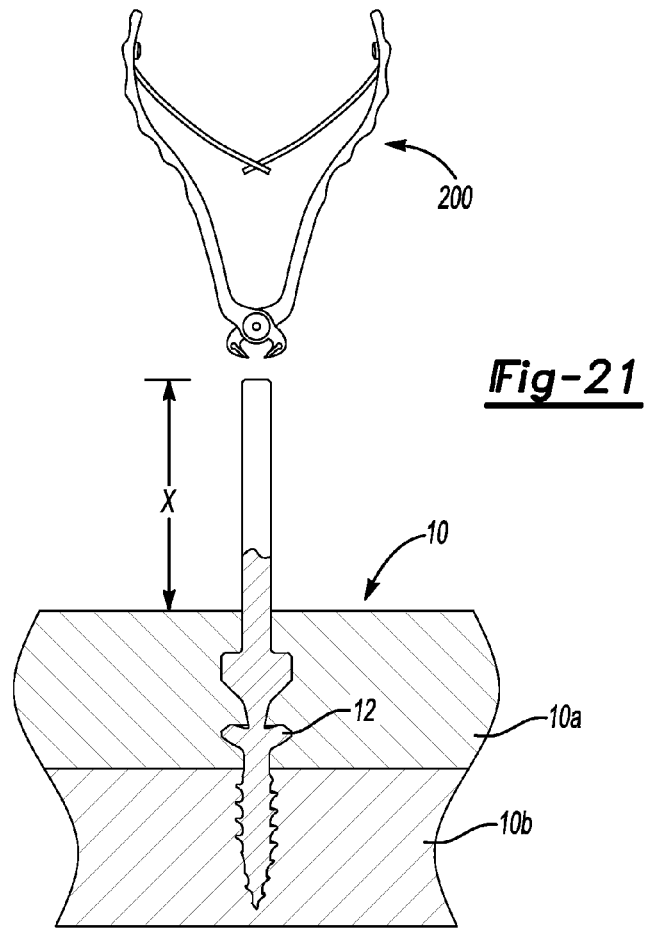
FIG. 21 illustrates a schematic representation of a surgical procedure for correcting a bone deformity employing a cannulated cutter

FIGS. 1, 16 and 21 illustrate a surgical procedure, such as an osteotomy to correct a bunion condition. In this procedure, a bone 10 is cut and realigned. An orthopedic fastener 12, such as a pin, screw, wire or the like, for example, is used to maintain bone segments 10a and 10b at the realigned position such that the bone 10 heals, and the bone deformity is corrected. An excess portion X of the orthopedic fastener 12 may protrude from the bone 10 and require trimming.

A torsion cutter 36 and 136 or a cannulated cutter 200 is utilized to remove the excess portion X of the orthopedic fastener 12. Although this disclosure and the examples illustrated herein are described relative to an osteotomy procedure, it should be understood that the example torsion cutter 36 and 136 or the cannulated cutter 200 may be utilized to perform a trimming task in any surgical procedure. In addition, the example torsion cutter 36 and 136 or the cannulated cutter 200 may be utilized to cut or trim any orthopedic fastener, including but not limited to, titanium pins, schanz screws and other similar orthopedic wires, etc.

Figure 2:
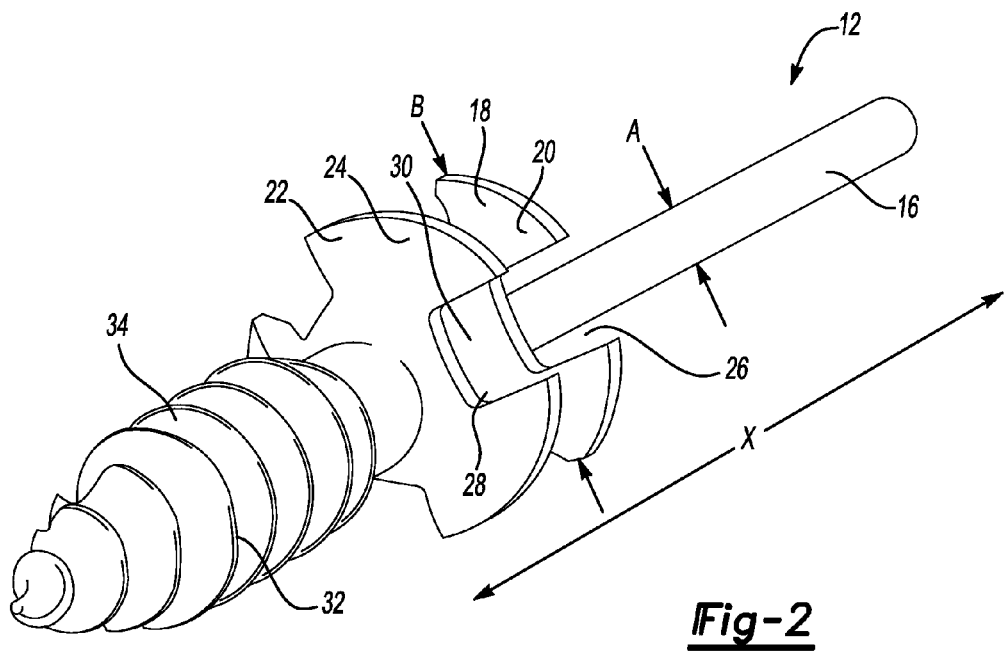
FIG. 2 illustrates a perspective view of an orthopedic fastener.

As shown in FIG. 2, the orthopedic fastener 12 includes a stem 16 having a diameter A, a first head 18 including a plurality of wings 20 defining a diameter B, and a second head 22 including a plurality of wings 24 defining a diameter B. The diameter B is greater than the diameter A. The wings 20 are separated by a space 26, and the wings 24 are separated by a space 28. In one example, there are three wings 20 and 24 and three spaces 26 and 28, and the wings 20 and 24 and the spaces 26 and 28 are equally spaced. In one example, each space 26 is aligned with one of the spaces 28 relative to the length of the excess portion X. A neck 30 (shown in FIG. 1) is defined between the heads 18 and 22. The orthopedic fastener 12 includes a threaded portion 32 including a plurality of threads 34 that extends from the second head 22 away from the stem 16. The threaded portion 32 is distal to the first head 18 such that the second head 22 is located between the threaded portion 32 and the first head 18. The orthopedic fastener 12 can have multiple sizes.

Figure 3:
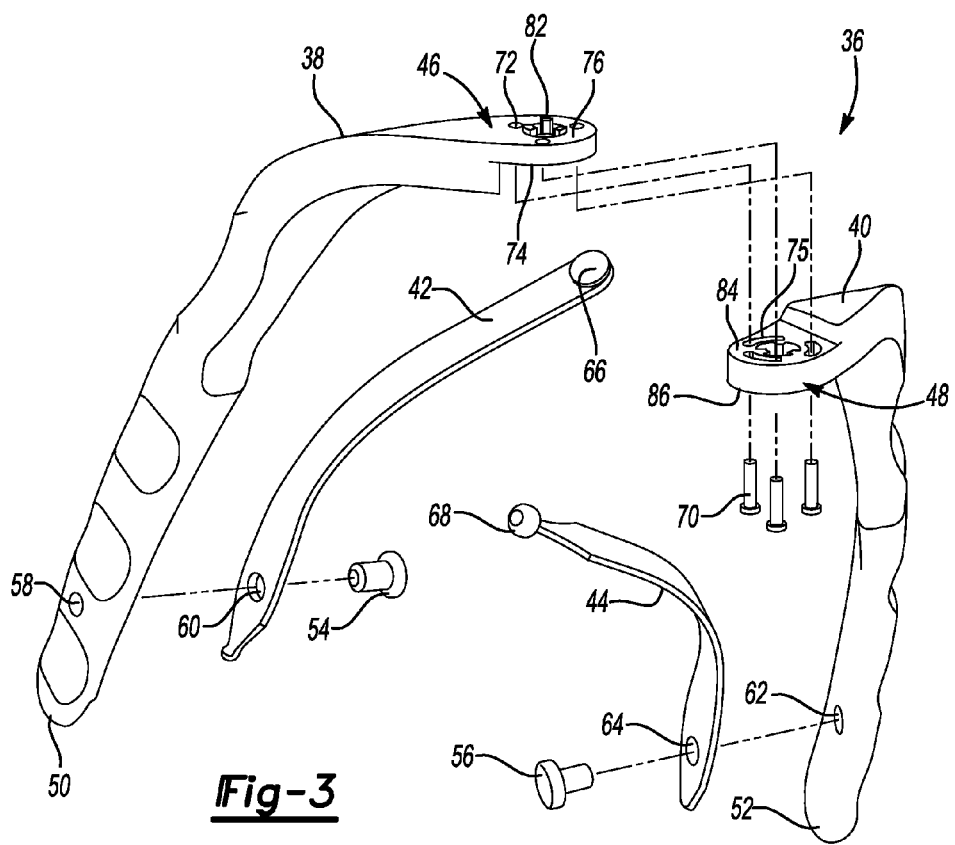
FIG. 3 illustrates an exploded view of the first embodiment torsion cutter.

FIG. 3 illustrates an exploded view of a first example torsion cutter 36 used to trim orthopedic fasteners 12 and the like during a surgical procedure. The torsion cutter 36 includes a first hand grip 38 and a second hand grip 40 that define a handle. A first leaf spring 42 and a second leaf spring 44 bias the hand grips 38 and 40, respectively, outwardly such that the torsion cutter 36 is in an open position (shown in FIG. 4). The first hand grip 38 and the second hand grip 40 both include a twisting portion 46 and 48, respectively, that are employed to trim the orthopedic fastener 12 by twisting. When the hand grips 38 and 40 are biased inwardly by applying a force F, the torsion cutter 36 moves from the open position (shown in FIG. 4) to a closed position (shown in FIG. 5) to trim the orthopedic fastener 12 and remove the excess portion X.

In one example, the components of the torsion cutter 36 (and the torsion cutter 136 described below) are made of a stainless steel material. However, a person of ordinary skill in the art would understand that other materials may be utilized to manufacture the components of the torsion cutter 36.

The leaf springs 42 and 44 are attached to an end portion 50 and 52 respectively, of the hand grips 38 and 40 by a fastener 54 and 56, respectively. The fastener 54 is received through aligned apertures 58 and 60 of the first hand grip 38 and the first leaf spring 42, respectively, and the fastener 56 is received through the aligned apertures 62 and 64 of the second hand grip 40 and the second leaf spring 44, respectively.

The first leaf spring 42 includes a socket 66, and the second leaf spring 44 includes a ball 68. The socket 66 is received in the ball 68. The ball 68 pivots in the socket 66 as the torsion cutter 36 moves between the open position shown in FIG. 4 and the closed position shown in FIG. 5. In another example, the first leaf spring 42 includes the ball 68, and the second leaf spring 44 includes the socket 66.

A plurality of fasteners 70 secure the first hand grip 38 and the second hand grip 40 together. Each fastener 70 is received in aligned openings 72 and 75 of the twisting portions 46 and 48, respectively, of the first hand grip 38 and the second hand grip 40, respectively. In one example, both the first hand grip 38 and the second hand grip 40 include three equally spaced openings 72 and 75, respectively. In one example, the openings 72 of the first hand grip 38 are substantially circular, and the openings 75 of the second hand grip 40 are substantially arc shaped. In another example, the openings 72 of the first hand grip 38 are substantially arc shaped, and the openings 75 of the second hand grip 40 are substantially circular. The openings 72 and 75 attach the first hand grip 38 and the second hand grip 40 to each other and also allow movement of the hand grips 38 and 40 relative to each other, as described below, as the torsion cutter 36 is moved between the open position (shown in FIG. 4) and the closed position (shown in FIG. 5) to remove the excess portion X of the orthopedic fastener 12.

FIG. 6 shows a side view of the first hand grip 38. The first hand grip 38 includes an inner surface 74 that faces the second hand grip 40 and an opposing outer surface 76 that faces the bone 10 during trimming of the orthopedic fastener 12.

FIG. 7 illustrates the inner surface 74 of the twisting portion 46 of the first hand grip 38, and FIG. 8 illustrates the outer surface 76 of the twisting portion 46 of the first hand grip 38. The twisting portion 46 includes a central opening 78 surrounded by a plurality of lobe shaped openings 80. In one example, the central opening 78 is substantially circular. In one example, there are three lobe shaped openings 80 that are equally spaced around the central opening 78. The number and orientation of the lobe shaped openings 80 correspond to the number and orientation of the wings 20 and 24. The central opening 78 and the lobe shaped openings 80 extend between the inner surface 74 to the outer surface 76. The lobe shaped openings 80 can accommodate a range of head sizes of the orthopedic fastener 12.

As shown in FIG. 9, the lobe shaped openings 80 are separated by a projection 82 that projects away from the outer surface 76 of the first hand grip 38. In one example, there are three projections 82 that are equally spaced around the central opening 78, and each projection 82 is located between two of the lobe shaped openings 80.

FIG. 10 illustrates a side view of the second hand grip 40. The second hand grip 40 includes an inner surface 84 that faces the first hand grip 38 and an opposing outer surface 86 that faces away from the bone 10 during cutting of the orthopedic fastener 12.

FIG. 11 illustrates the inner surface 84 of the twisting portion 48 of the second hand grip 40, and FIG. 12 illustrates the outer surface 86 of the twisting portion 48 of the second hand grip 40. The twisting portion 48 includes a central opening 88. In one example, the central opening 88 is substantially circular. The central openings 78 and 88 of the hand grips 38 and 40, respectively, are aligned when the torsion cutter 36 is in both the open position and the closed position.

The inner surface 84 of the twisting portion 48 includes a plurality of lobe shaped openings 90 that surround the central opening 88. In one example, there are three lobe shaped openings 90 equally spaced around the central opening 88.

The number and orientation of the lobe shaped openings 90 correspond to the number and orientation of the wings 20 and 24 of the orthopedic fastener 12 and the lobe shaped openings 80. The outer surface 86 of the twisting portion 48 does not include the plurality of lobe shaped openings 90. That is, each of the plurality of lobe shaped openings 90 define a blind hole. The lobe shaped openings 90 can accommodate a range of head sizes of the orthopedic fastener 12.

Returning to FIG. 10, the plurality of lobe shaped openings 90 extend only partially from the inner surface 84 to the outer surface 86 of the twisting portion 48 of the second hand grip 40, defining a shoulder 92 (a blind hole) that acts as a stop for the first head 18 of the orthopedic fastener 12.

Figure 13:
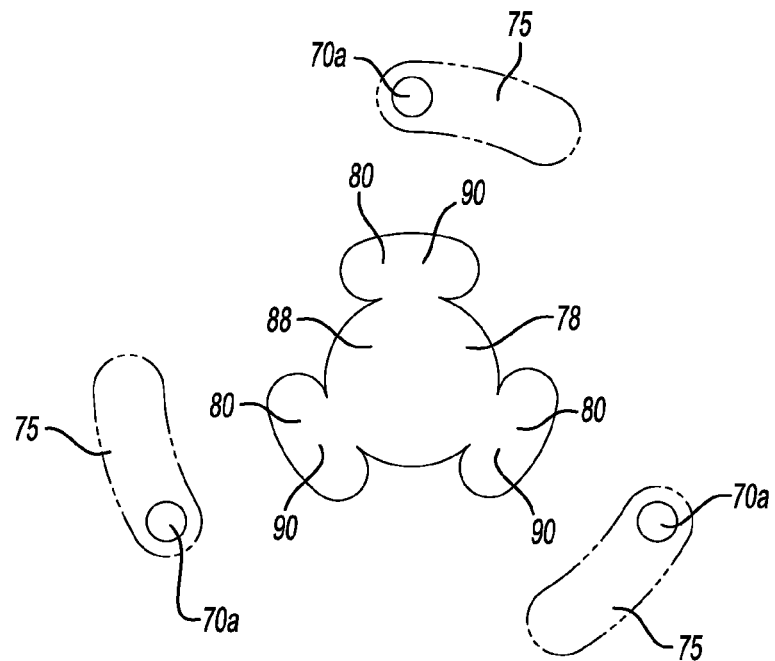
FIG. 13 illustrates a twisting mechanism of the first embodiment torsion cutter in the open position.
Figure 14:
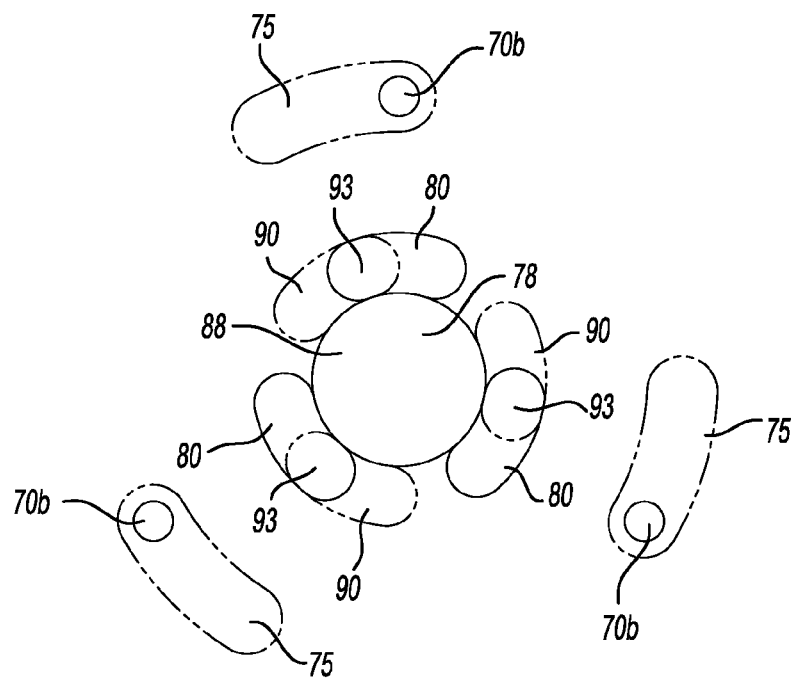
FIG. 14 illustrates the twisting mechanism of the first embodiment torsion cutter in the closed position.

FIG. 13 illustrates the twisting mechanism when the torsion cutter 36 is in the open position, and FIG. 14 illustrates the twisting mechanism when the torsion cutter 36 is in the closed position. As shown in FIG. 13, when the torsion cutter 36 is in the open position, each lobe shaped opening 80 of the first hand grip 38 is aligned with one lobe shaped opening 90 of the second hand grip 40.

The torsion cutter 36 is positioned such that the first hand grip 38 faces the bone 10 while in the open position to trim the orthopedic fastener 12. The stem 16 is inserted into the aligned central openings 78 and 88 of the torsion cutter 36, and the torsion cutter 36 is slid relative to the stem 16 such that the stem 16 slides through the aligned central openings 78 and 88.

The wings 20 of the first head 18 pass through the lobe shaped openings 80 of the first hand grip 38 and into the lobe shaped openings 90 of the second hand grip 40. The torsion cutter 36 continues to slide until the first head 18 of the orthopedic fastener 12 contacts the shoulder 92 of the second hand grip 40, preventing further movement of the torsion cutter 36 towards the bone 10, as shown in FIG. 1. As the diameter B of the first head 18 is greater than the diameter A of the stem 16, the first head 18 does not pass through the aligned central openings 78 and 88.

Each projection 82 of the first hand grip 38 is received in one of the spaces 28 (that is, between two adjacent wings 24) of the second head 22 of the orthopedic fastener 12, retaining the first hand grip 38 of the torsion cutter 36 relative to the orthopedic fastener 12. That is, the first hand grip 38 is immobile relative to the second head 22 of the orthopedic fastener 12. Each wing 20 of the first head 18 of the orthopedic fastener 12 is received in one lobe shaped opening 90 of the second hand grip 40. Returning to FIG. 13, when the torsion cutter 36 is in the open position, the fasteners 70 are in the position 70A relative to the openings 75.

The inwardly force F is then applied to the hand grips 38 and 40 to position the torsion cutter 36 in the closed position, pivoting the second hand grip 40 relative to the first hand grip 38 and twisting the second head 22 of the orthopedic fastener 12. As the projections 82 of the first hand grip 38 are received between the spaces 28 of the second head 22 of the orthopedic fastener 12, the first hand grip 38 does not move relative to the orthopedic fastener 12. The fasteners 70 located in the circular openings 72 of the first hand grip 38 are retained in the same position relative to the first hand grip 38. As the torsion cutter 36 moves to the closed position (that is, as the second hand grip 40 moves), the arc shaped openings 75 slide around the fasteners 70 to allow the second hand grip 40 to pivot relative to the first hand grip 38 such that the fasteners 70 are located in the position 70B (shown in FIG. 14).

Figure 15:
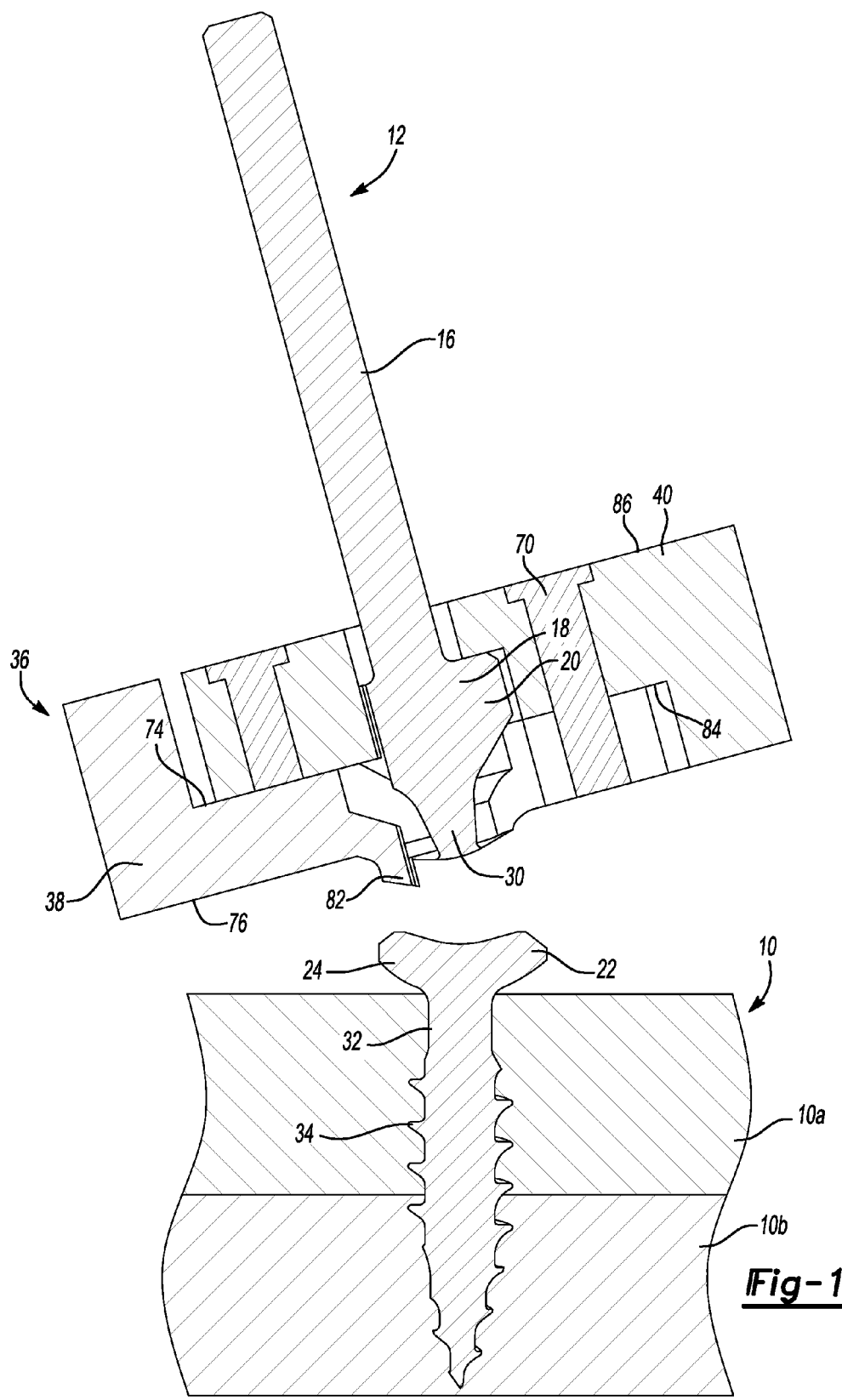
FIG. 15 illustrates a schematic representation of the surgical procedure after removal of a post of the orthopedic fastener with the first embodiment torsion cutter.

As the second hand grip 40 pivots about a rotational axis, the lobe shaped openings 90 move with respect to the lobe shaped openings 80, reducing the size of a space 93 defined by the lobe shaped openings 80 and 90. The wings 20 of the first head 18 of the orthopedic fastener 12 that are retained in the lobe shaped openings 90 of the twisting portion 48 of the second hand grip 40 also rotate with the second hand grip 40, while the threaded portion 32 of the orthopedic fastener 12 is retained in the bone 10 and the first head 22 remains stationary. The rotational axis of the torsion cutter 36 is aligned with a central axis of the orthopedic fastener 12. A twisting force or torque is applied to the neck 30 of the orthopedic fastener 12, breaking the neck 30 to remove the stem 16 and the first head 18 from the second head 22 and the threaded portion 32 (the excess portion X), as shown in FIG. 15. The twisting action removes the stem 16 from the second head 22 without leaving a burr on the surface above the second head 22, providing a smooth surface that does not require any further smoothing process.

Figure 17:
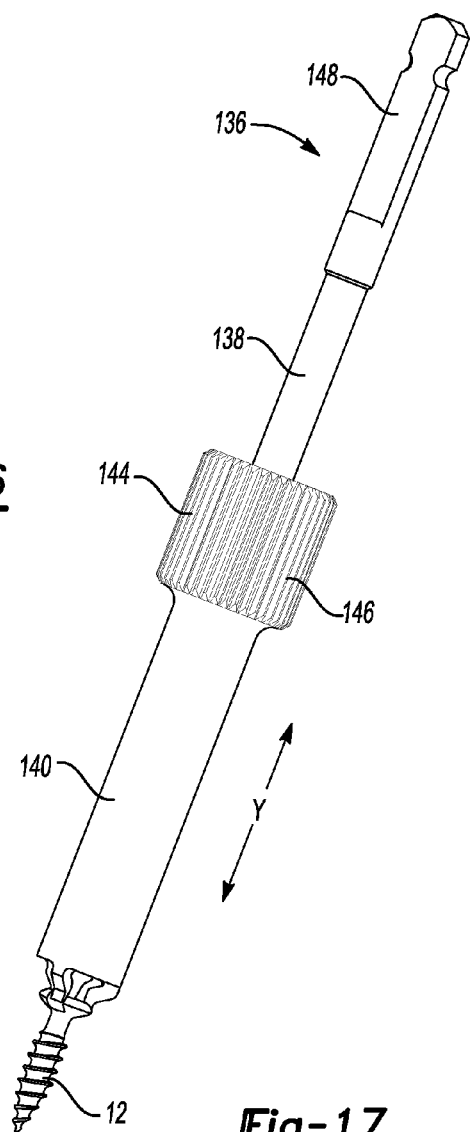
FIG. 17 illustrates a perspective view of the second embodiment torsion cutter.

FIGS. 16 and 17 illustrate the second example torsion cutter 136. The torsion cutter 136 includes a drive shaft 138 received in a cylindrical passage 142 of a cutter sleeve 140. The cutter sleeve 140 includes a grip 144 including a plurality of ribs 146 that assist an operator in holding the cutter sleeve 140. The drive shaft 138 includes a grasping portion 148 that can be turned by the operator. The drive shaft 138 also includes a cylindrical passage 159 that receives the stem 16 of the orthopedic fastener 12. The drive shaft 138 can be rotated relative to the cutter sleeve 140 about an axis Y to remove the excess portion X of the orthopedic fastener 12.

The torsion cutter 136 also includes an alignment feature that aligns the drive shaft 138 relative to the cutter sleeve 140. In one example, one end of a spring 192 is attached to a wall of the cylindrical passage 142 of the cutter sleeve 140, and a ball bearing 190 is attached to the opposing end of the spring 192. The drive shaft 138 includes a circular ring 196 that is substantially perpendicular to the axis Y. The circular ring 196 ensures that the cutter sleeve 136 is located at the correct depth with respect to the underside of the second head 22. The circular ring 196 also includes two opposing circular grooves 194 that are 180° apart. When the drive shaft 138 is properly aligned relative to the cutter sleeve 140, the ball bearing 190 is received in one of the grooves 194 to provide rotational alignment of the drive shaft 138 relative to the cutter sleeve 140.

Figure 18:
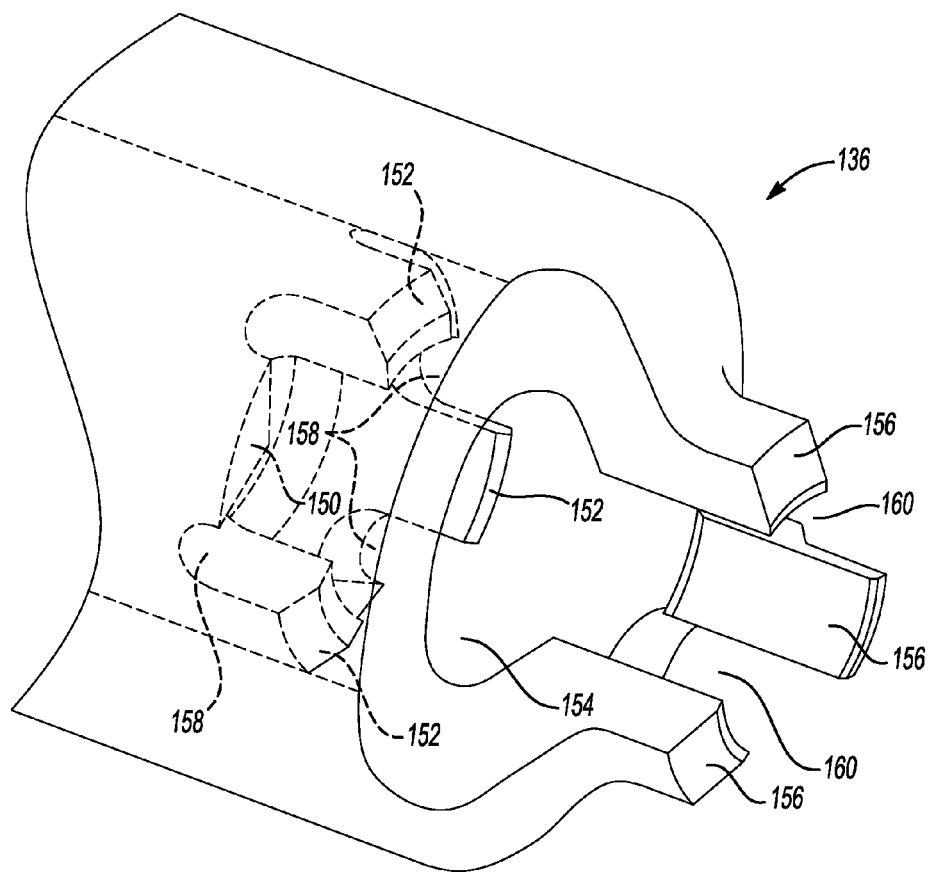
FIG. 18 illustrates an end of the second embodiment torsion cutter.

As shown in FIG. 18, an end of the drive shaft 138 opposite to the grasping portion 148 includes a surface 150 and a plurality of projections 152 that extend or project away from the surface 150. The number and orientation of the projections 152 correspond to the number and orientation of the spaces 26 of the first head 18 of the orthopedic fastener 12. A space 158 is defined between two adjacent projections 152. In one example, there are three projections 152 and three spaces 158, and the projections 152 and the spaces 158 are equally spaced.

An end of the cutter sleeve 140 opposite to the grip 144 includes an interior space 154 and a plurality of projections 156. A portion of the drive shaft 138 is received in the interior space 154 of the cutter sleeve 140, and a portion of the drive shat 138 (the grasping portion 148) extends out of the cutter sleeve 140 such that it is accessible by the user.

The number and orientation of the projections 156 correspond to the number and orientation of the spaces 26 and 28 of the heads 18 and 22, respectively, of the orthopedic fastener 12. A space 160 is defined between two adjacent projections 156. In one example, there are three projections 156 and three spaces 160, and the projections 156 and the spaces 160 are equally spaced. When the torsion cutter 136 is in a first position, the projections 152 and 156 are aligned relative to the axis Y. That is, each of the projections 152 are aligned with one of the projections 156.

The torsion cutter 136 is positioned such that the projections 156 of the cutter sleeve 140 face the bone 10. The stem 16 of the orthopedic fastener 12 is first inserted between the projections 156 of the cutter sleeve 140. The torsion cutter 136 is then moved towards the bone 10 such that the stem 16 of the orthopedic fastener 12 slides within cylindrical passage 159 of the drive shaft 138. The plurality of wings 20 of the first head 18 are each temporary received in one the spaces 160 between the projections 156 of the cutter sleeve 140, and each of the projections 156 are each received in one of the spaces 26 of the first head 18. The torsion cutter 136 continues to slide towards the bone 10, and the first head 18 moves towards the surface 150 of the drive shaft 138.

Figure 19:
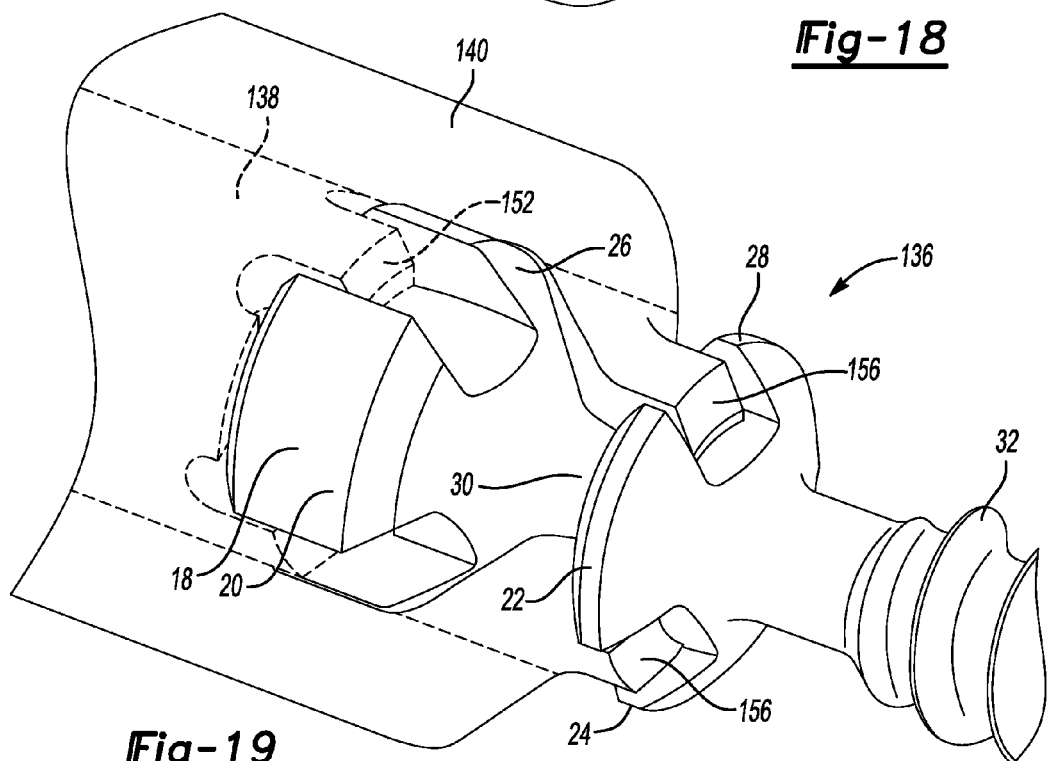
FIG. 19 illustrates the end of the second embodiment torsion cutter receiving the orthopedic fastener.

The drive shaft 138 may need to be rotated about the axis Y to ensure that the projections 152 of the drive shaft 138 can each be received within one of the spaces 26 of the first head 18. The contact of the first head 18 with the surface 150 prevents further movement of the torsion cutter 136 towards the bone 10. Once the torsion cutter 136 receives the orthopedic fastener 12, the torsion cutter 136 is in the first position, as shown in FIG. 19. The projections 156 of the cutter sleeve 140 are each received within one of the spaces 28 of the second head 22, and the projections 152 of the drive shaft 138 are each received within one of the spaces 26 of the first head 18. The first head 18 is received in the interior space 154 of the cutting sleeve 140. As stated above, the drive shaft 138 may need to be rotated slightly about the axis Y to ensure that the projections 152 are received in the spaces 26 of the first head 18.

The excess portion X of the orthopedic fastener 12 is removed by rotating the drive shaft 138 relative to the cutter sleeve 140 about the axis Y. As the operator holds the grip 144 of the cutter sleeve 140 to maintain the cutter sleeve 140 stationary, the operator can turn the grasping portion 148 to rotate the drive shaft 138 about the axis Y relative to the cutter sleeve 140 to a second position.

As the torsion cutter 136 is rotated to the second position about the axis Y, the first head 18 of the orthopedic fastener 12 rotates due to the engagement of each of the projections 152 within one of the spaces 26 of the first head 18. The cutter sleeve 140 and the second head 22 remain stationary due to the engagement of the projections 156 in the spaces 28 of the second head 22. The axis Y is aligned with a central axis of the orthopedic fastener 12.

Figure 20:
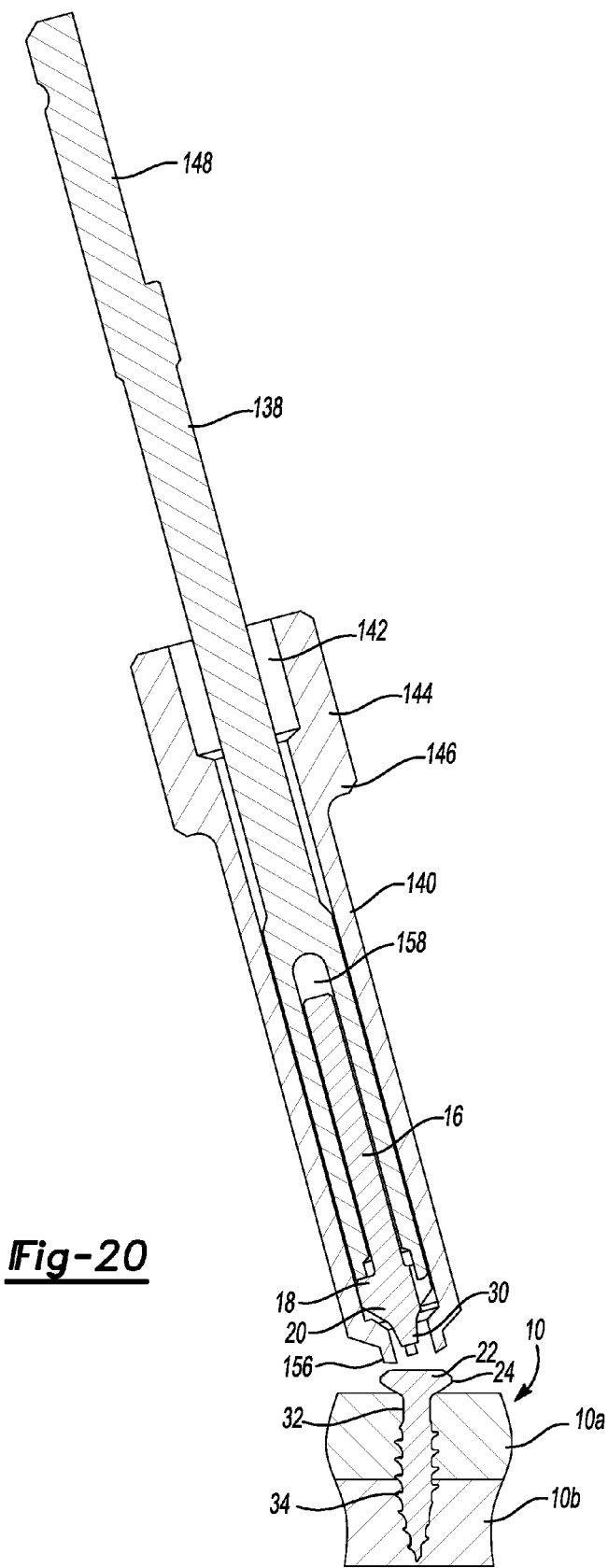
FIG. 20 illustrates a schematic representation of the surgical procedure after removal of a post of the orthopedic fastener with the second embodiment torsion cutter.

As the drive shaft 138 rotates, the first head 18 of the orthopedic fastener 12 rotates, and a twisting or torsional force or torque is applied to the neck 30 of the orthopedic fastener 12, breaking the neck 30 to remove the stem 16 and the first head 18 from the second head 22 and the threaded portion 32, as shown in FIG. 20. The twisting action removes the stem 16 from the second head 22 without leaving a burr on the upper surface of the second head 22, providing a smooth surface that does not require any further smoothing process.

Figure 23:
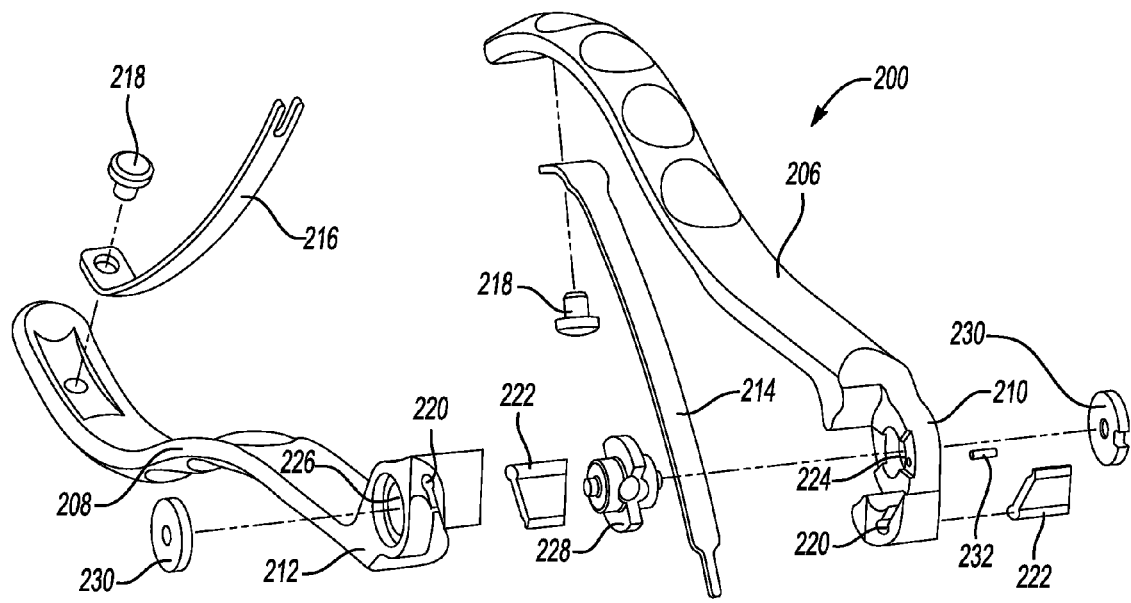
FIG. 23 illustrates a general assembly view of the cannulated cutter.
Figure 22:
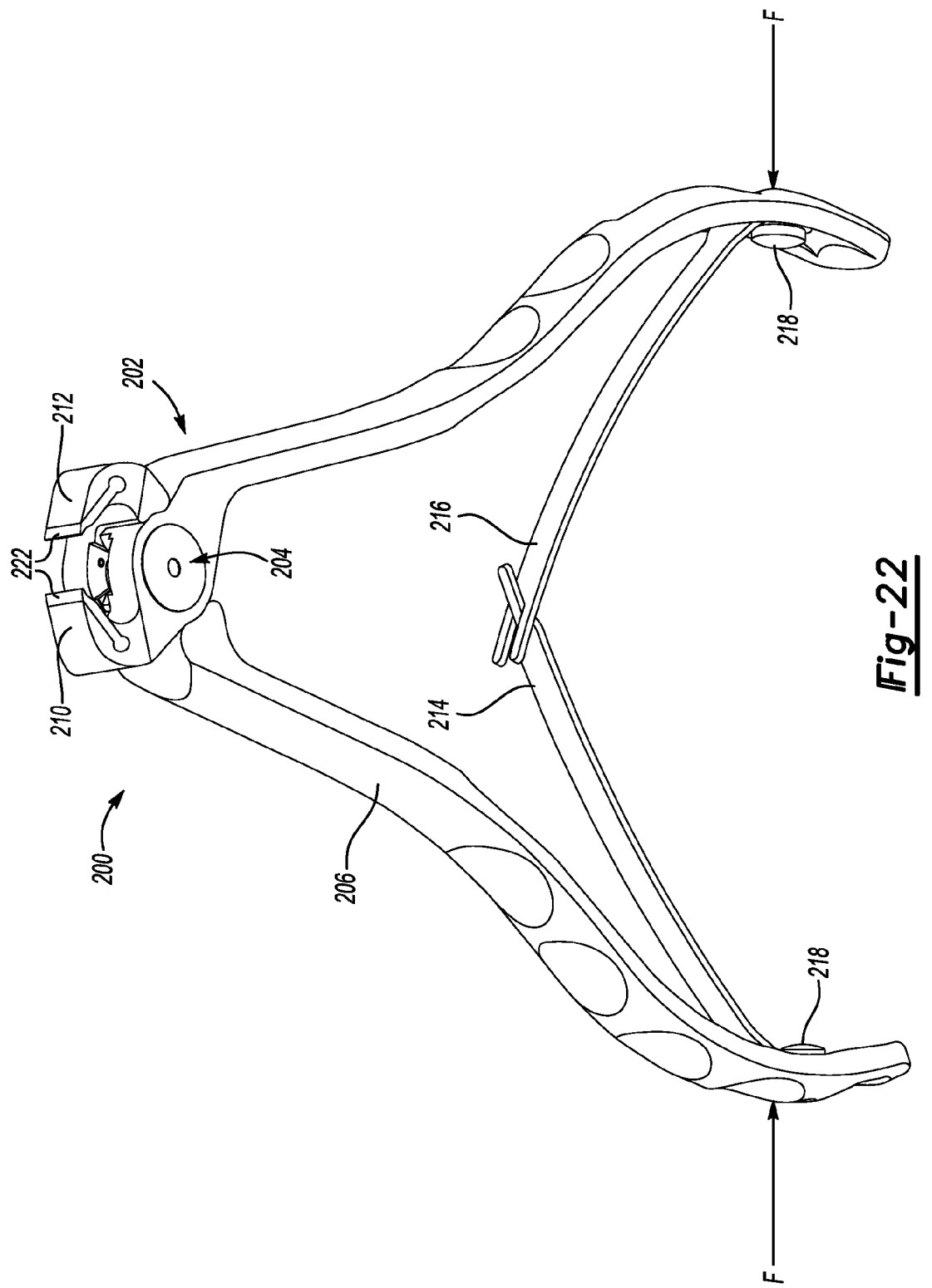
FIG. 22 illustrates a schematic view of the cannulated cutter.

FIGS. 21, 22 and 23 illustrate an example cannulated cutter 200 utilized to trim the excess portion X of the orthopedic fastener 12. The cannulated cutter 200 includes a handle assembly 202 and a cannulation assembly 204. The handle assembly 202 includes two hand grips 206 and 208 and opposing jaws 210 and 212. In one example, the jaws 210 and 212 are formed integrally with the hand grips 206 and 208 at a distal end thereof. A pair of leaf springs 214 and 216 bias the hand grips 206 and 208 outwardly such that the jaws 210 and 212 are in an open position. The cannulated cutter 200 is prepared to cut or trim the orthopedic fastener 12 when the jaws 210 and 212 are positioned in the open position.

In one example, the components of the handle assembly 202 and the cannulation assembly 204 are made of a stainless steel material. However, a person of ordinary skill in the art would understand that other materials may be utilized to manufacture the components of the handle assembly 202 and the cannulation assembly 204.

The hand grips 206 and 208 are squeezed by applying a force F to close the jaws 210 and 212 and cut/trim the orthopedic fastener 12. The leaf springs 214 and 216 are attached to the hand grips 206 and 208 adjacent a proximal end thereof via fasteners 218.

Each jaw 210 and 212 of the cannulated cutter 200 includes a groove 220 for receiving a cutting tip 222 (See FIG. 24). In one example, the cutting tips 222 are made of a different material than the other components of the handle assembly 202. In one example, the cutting tips 222 are made of a tungsten carbide material. In another example, the cutting tips 222 include an alloy steel. It should be understood that other materials may be utilized to manufacture the example cutting tips 222.

The jaws 210 and 212 include openings 224 and 226 for receiving the cannulation assembly 204. That is, the cannulation assembly 204 is an independent and distinct component from the handle assembly 202. The cannulation assembly 204 includes a swivel pin 228, caps 230 and a dowel pin 232. The cannulation assembly 204 provides for cannulation of the cannulated cutter 200. That is, the cannulation assembly 204 creates a passage through the cannulated cutter 200 for receiving the excess portion X of the orthopedic fastener 12 between the jaws 210 and 212. The excess portion X of the orthopedic fastener 12 may be cut or trimmed with the cannulated cutter 200, as is further described below.

Figure 26:
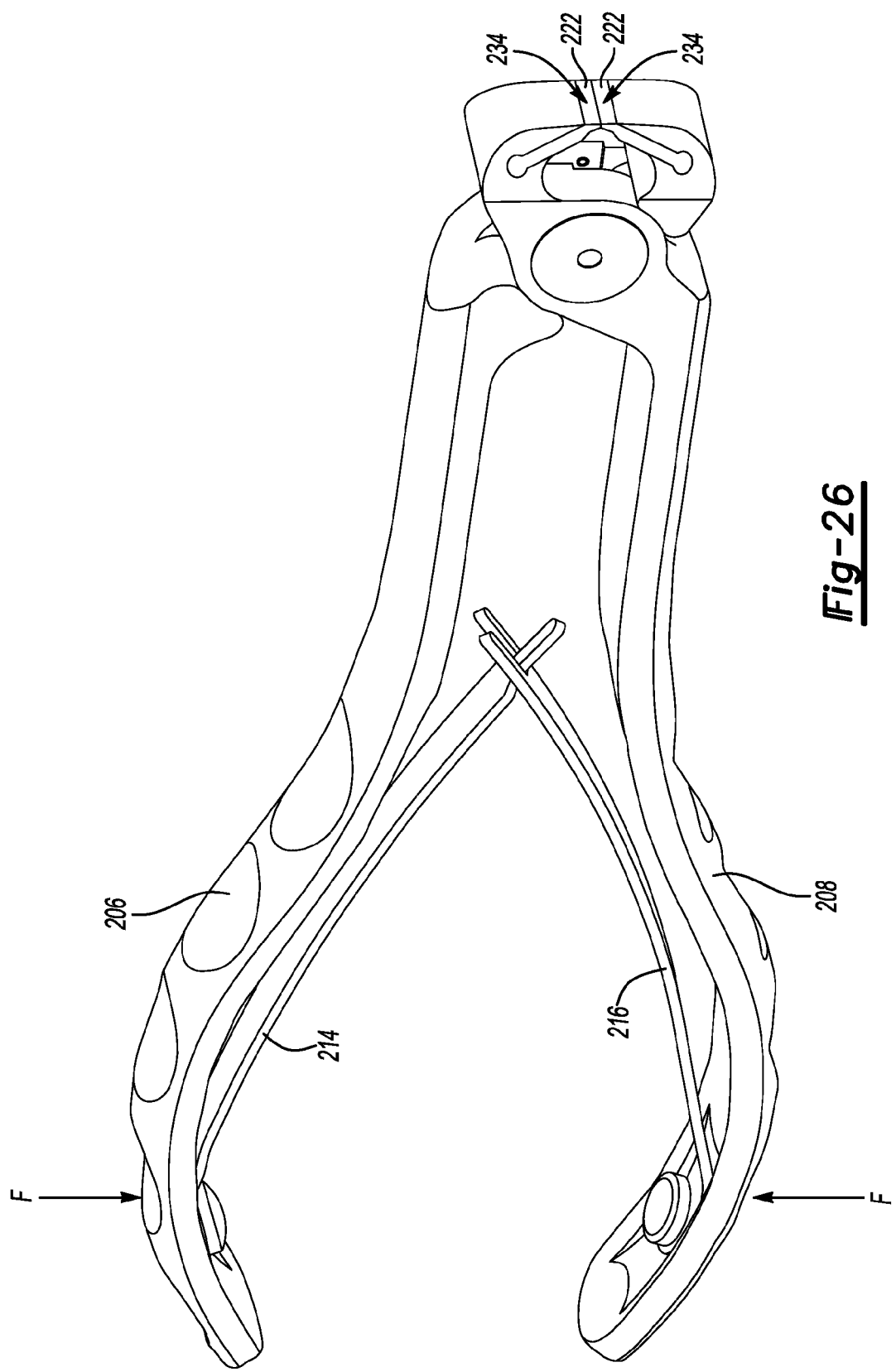
FIG. 26 illustrates another schematic view of the cannulated cutter.

FIG. 25 illustrates an example cutting tip 222 of the cannulated cutter 200. Each jaw 210 and 212 of the cannulated cutter 200 receives a cutting tip 222. The cutting tips 222 define an edge thickness 234 at a distal end 236 and a tongue portion 238 at a proximal end 240 of the cutting tip 222. The tongue portion 238 of each cutting tip 222 is received within the groove 220 of each jaw 210 and 212 via an interference fit, for example. The edge thicknesses 234 of the cutting tips 222 contact one another to facilitate a near flush cut of an orthopedic fastener 12 where the hand grips 206 and 208 of the cannulated cutter 200 are squeezed together in the F direction (see FIG. 26).

In one example, the edge thickness 234 of each cutting tip 222 does not include a beveled or chamfered surface. Instead, the edge thickness 234 defines a generally straight edge having a substantially constant thickness. The shape and thickness of the edge thicknesses 234 allow the cutting tips 222 to leave a minimal burr when used to cut the orthopedic fastener 12. In one example, the edge thickness 234 of each cutting tip 222 is about 0.010 inches. The term "about" as utilized within this disclosure is intended to define the example dimensions of the edge thickness 234 as including a general range of tolerance. A person of ordinary skill in the art having the benefit of this disclosure would understand that variations in the dimensions disclosed herein are contemplated as within the scope of this disclosure.

Figure 28:
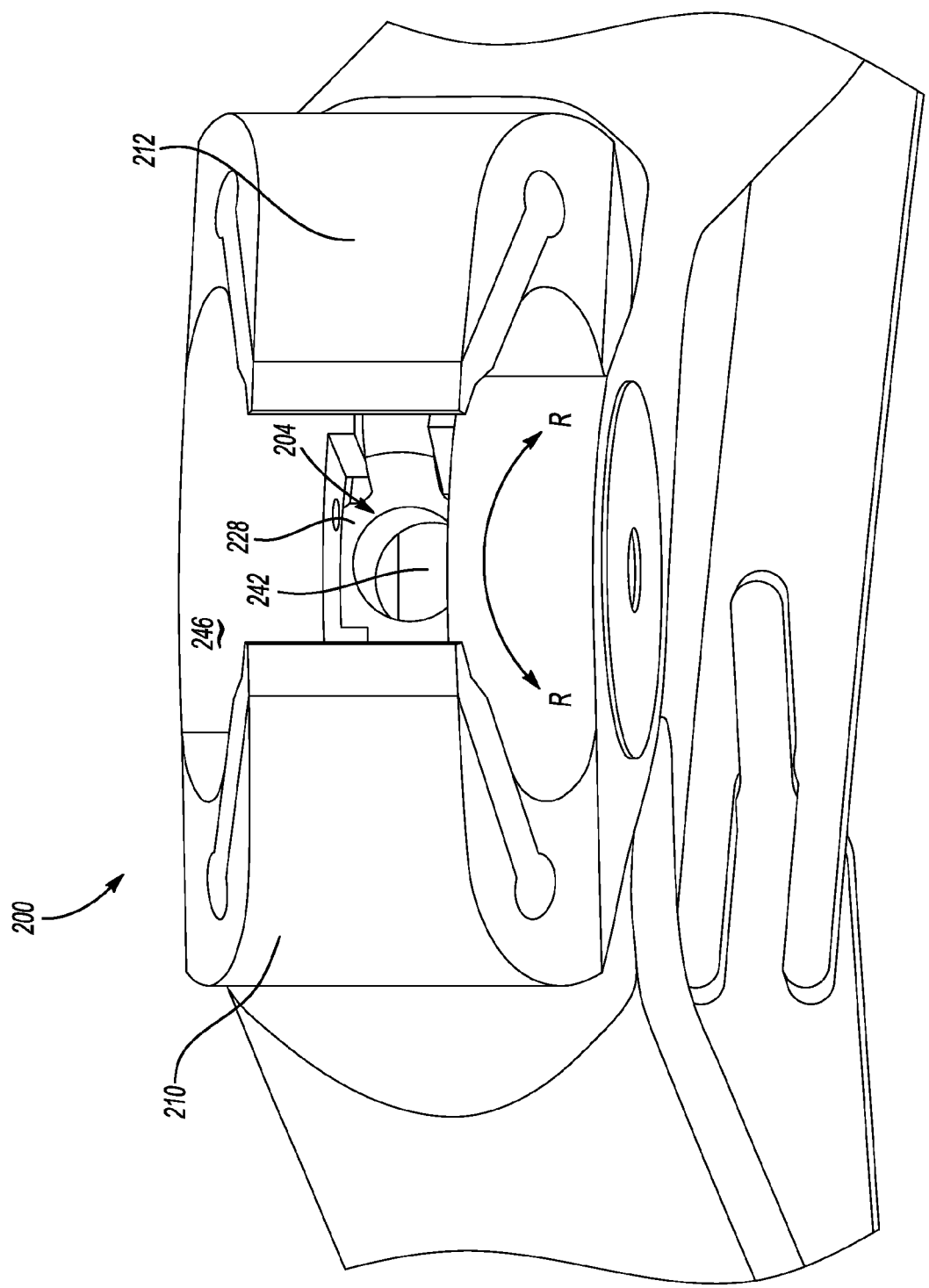
FIG. 28 illustrates a schematic view of the cannulated cutter.

FIG. 27 illustrates the swivel pin 228 of the cannulation assembly 204 of the cannulated cutter 200. The swivel pin 228 includes an aperture 242 that extends between circular shoulders 244. The aperture 242 of the swivel pin 228 extends through the entire thickness of the swivel pin 228. In one example, the aperture 242 extends from a jaw side 246 to the hand grip side 248 of the cannulated cutter 200 where the swivel pin 228 is received within the openings 224 and 226 of the jaws 210 and 212 (See FIGS. 28 and 29).

Figure 29:
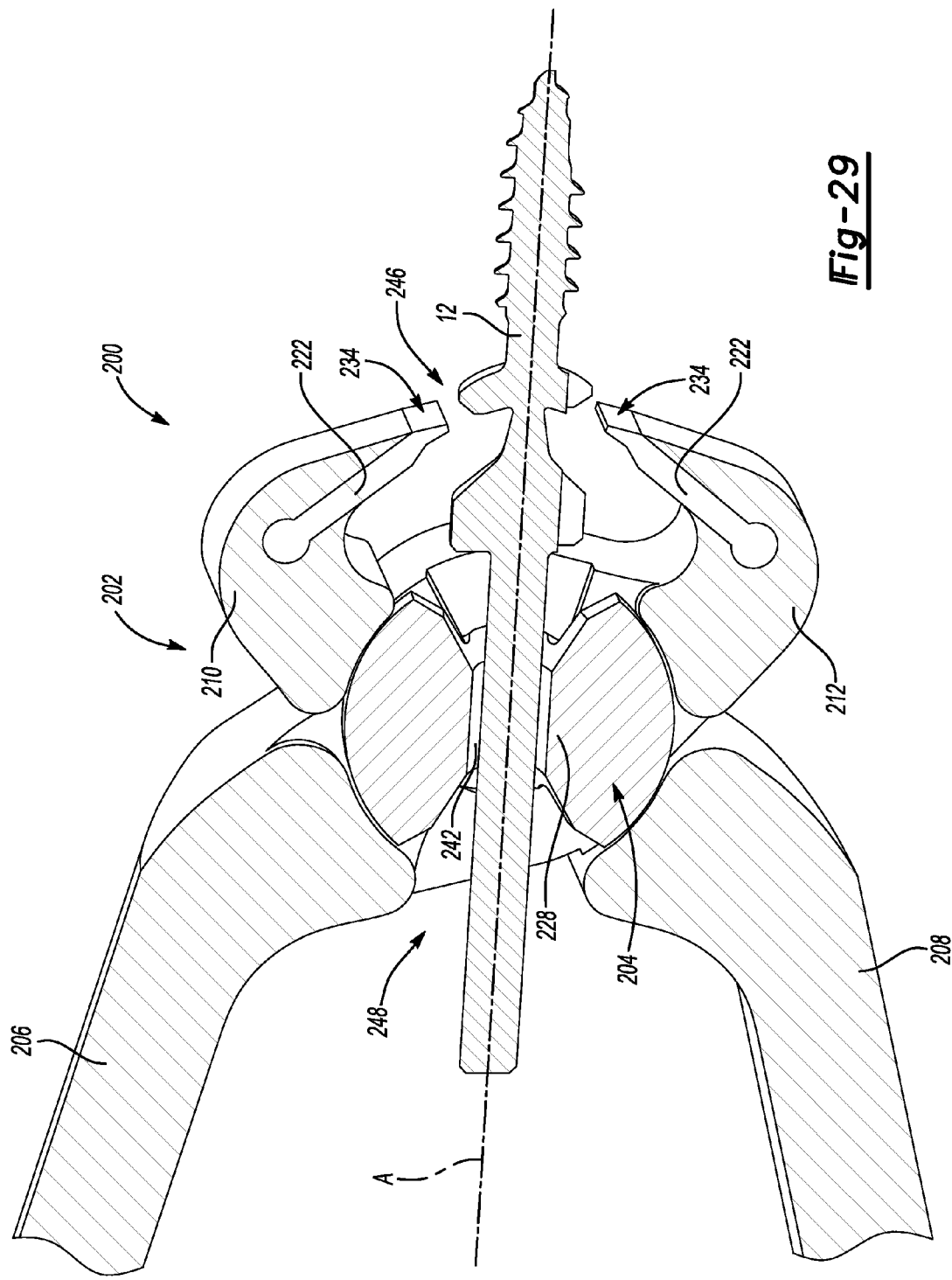
FIG. 29 illustrates the cannulated cutter receiving the orthopedic fastener for cutting or trimming the orthopedic fastener.

The aperture 242 is generally aligned with the jaws 210 and 212 and is positioned such that the aperture 242 is axially aligned with a longitudinal axis A of the orthopedic fastener 12 to cut or trim a portion of the orthopedic fastener 12 (see FIG. 29). Because the aperture 242 extends through the entire thickness of the swivel pin 228, the assembled cannulated cutter 200 is considered cannulated for receiving a portion of an orthopedic fastener 12. The cannulated cutter 200 is slideable over a portion of an orthopedic fastener 12 that protrudes from a bone and is operable to provide a near flush cut of the excess portion while leaving a minimal burr or no burr on the orthopedic fastener 12. The cut portion of the orthopedic fastener 12 is temporarily held inside the swivel pin 228 post-cut.

The circular shoulders 244 of the swivel pin 228 are received within the openings 224 and 226 of the jaws 210 and 212 to selectively attach the cannulation assembly 204 to the handle assembly 202 and to assemble the cannulated cutter 200. The caps 230 are inserted over the circular shoulders 244 and receive pins 250 that protrude from the circular shoulders 244. Therefore, the swivel pin 228 is mounted to the caps 230 and is rotatable independently of the handle assembly 202. A dowel pin 232 secures the swivel pin 228 relative to the caps 230 (See FIG. 23).

The swivel pin 228 is positioned relative to the jaws 210 and 212 such that the aperture 242 faces in the direction of the jaw side 246. In one example, the swivel pin 228 has a generally circular range of motion in a direction R-R of about 10 degrees relative to the jaws 210 and 212 (See FIG. 28). However, the actual range of motion of the swivel pin 228 will vary depending upon design specific parameters including, but not limited to, the size and shape of the handle assembly 202. The cannulation assembly 204 is capable of receiving a portion of an orthopedic fastener 12, regardless of the position or orientation of the jaws 210 and 212.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A surgical instrument assembly comprising:
an orthopedic fastener; and
a surgical instrument comprising a first component and a second component rotatable relative to the first component between a first position and a second position about a rotational axis, wherein rotation of the second component from the first position to the second position applies a force to the orthopedic fastener to remove a portion of the orthopedic fastener, wherein a central axis of the orthopedic fastener is aligned with the rotational axis; and
wherein the orthopedic fastener includes a stem received in a cylindrical passage of the second component, a first head with a plurality of spaced apart first wings, a second head with a plurality of spaced apart second wings, a neck defined between the first head and the second head, and a threaded portion, wherein the second head is located between the first head and the threaded portion, the surgical instrument applies the force at the neck of the orthopedic fastener to remove the portion of the orthopedic fastener, and the portion includes the stem and the first head.

2. The surgical instrument assembly as recited in claim 1 wherein the first component is a cylindrical sleeve and the second component is a drive shaft received in the cylindrical sleeve.

3. The surgical instrument assembly as recited in claim 2 wherein the drive shaft includes a plurality of drive shaft projections and the cylindrical sleeve includes a plurality of sleeve projections, wherein a drive shaft space is defined between two adjacent of the plurality of drive shaft projections and a sleeve space is defined between two adjacent of the plurality of sleeve projections.

4. The surgical instrument assembly as recited in claim 3 wherein the plurality of sleeve projections and the plurality of drive shaft projections are aligned when the drive shaft is in the first position and are non-aligned with the drive shaft is in the second position.

5. The surgical instrument assembly as recited in claim 1 wherein the first component is a first hand grip that includes a first twisting portion having a first central opening and the second component is a second hand grip that includes a second twisting portion having a second central opening, and the orthopedic fastener is received in the aligned first central opening and the second central opening.

6. The surgical instrument assembly as recited in claim 5 wherein an attachment feature is received in a first attachment opening of the first twisting portion and a second attachment opening of the second twisting portion to connect the first twisting portion to the second twisting portion, wherein one of the first attachment opening and the second attachment opening is substantially circular and the other of the first attachment opening and the second attachment opening is arc shaped.

7. The surgical instrument assembly as recited in claim 5 wherein the first central opening includes a plurality of first lobe shaped openings that extend entirely through a first width of the first twisting portion and the second central opening includes a plurality of second lobe shaped openings that defines a blind hole that extend partially through a second width of the second twisting portion.

8. The surgical instrument assembly as recited in claim 7 wherein each of the plurality of spaced apart first wings are received in one of the plurality of second lobe shaped openings and each of the plurality of spaced apart second wings are received in one of the plurality of first lobe shaped openings, and the second hand grip is rotated relative to the first hand grip from the first position to the second position to twist the orthopedic fastener at the neck and remove the portion of the orthopedic fastener.

9. The surgical instrument assembly as recited in claim 7, wherein each of the plurality of spaced apart first wings are received in one of the plurality of second lobe shaped openings and each of the plurality of spaced apart second wings are received in one of the plurality of first lobe shaped openings, and the second hand grip is rotated relative to the first hand grip from the first position to the second position to twist the orthopedic fastener at the neck and remove the portion of the orthopedic fastener.

10. The surgical instrument assembly as recited in claim 9 wherein the plurality of first shaped lobe shaped openings are separated by a projection that projects from an outer surface of the first twisting portion, and each of the projections are received between the adjacent spaced apart second wings of the orthopedic fastener to prevent rotation of the first component as the second component is moved to the second position.

11. The surgical instrument assembly as recited in claim 1 wherein the force is a torsional force.

12. The surgical instrument assembly as recited in claim 1 wherein removal of the portion of the orthopedic fastener provides no burr once the portion is removed.

13. The surgical instrument assembly as recited in claim 1 wherein the second component includes a groove, a resilient member is attached to the first component, and the resilient member is received in the groove to align the second component relative to the first component.

14. The surgical instrument assembly as recited in claim 1 wherein a portion of the second component that extends from the first component does not include an internal passage.

15. The surgical instrument assembly as recited in claim 1 wherein the second component is longer than the first component.

* * * * *